United States Patent [19]

Zink et al.

[11] Patent Number: 5,162,550

[45] Date of Patent: Nov. 10, 1992

[54] BISPHTHALIDE LACTONES, THEIR PREPARATION AND THE USE THEREOF IN RECORDING MATERIALS

[75] Inventors: Rudolf Zink, Therwil; Ian J. Fletcher, Magden, both of Switzerland

[73] Assignee: Ciba-Geigy Corporation, Ardsley, N.Y.

[21] Appl. No.: 572,929

[22] Filed: Aug. 24, 1990

[30] Foreign Application Priority Data

Aug. 29, 1989 [CH] Switzerland .................. 3126/89

[51] Int. Cl.⁵ ................. C07D 321/12; C07D 30/77
[52] U.S. Cl. ....................... 549/265; 549/264; 549/304; 549/307; 549/310; 544/60; 544/148; 544/230; 546/15; 546/89; 546/116; 548/407; 548/510
[58] Field of Search ............ 549/307, 310, 264, 265, 549/304; 503/220; 546/116, 89, 15; 544/350, 345, 148, 60, 230; 548/510, 407

[56] References Cited

U.S. PATENT DOCUMENTS

| | | |
|---|---|---|
| 4,277,400 | 7/1981 | Garner et al. .................. 548/493 |
| 4,381,266 | 4/1983 | Garner et al. .................. 562/887 |

FOREIGN PATENT DOCUMENTS

| | | |
|---|---|---|
| 0112710 | 7/1984 | European Pat. Off. . |
| 0156250 | 10/1985 | European Pat. Off. . |
| 0176161 | 4/1986 | European Pat. Off. . |
| 1277862 | 9/1968 | Fed. Rep. of Germany . |
| 2937525 | 3/1981 | Fed. Rep. of Germany . |
| 3618562 | 12/1986 | Fed. Rep. of Germany . |

*Primary Examiner*—Richard L. Raymond
*Assistant Examiner*—Shailendra Kumar
*Attorney, Agent, or Firm*—Marla J. Mathias; Edward McC. Roberts

[57] ABSTRACT

Bisphthalide lactones of formula

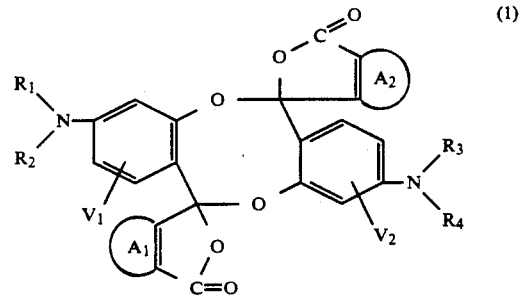

wherein $R_1$, $R_2$, $R_3$ and $R_4$ are each independently of one another hydrogen, alkyl of at most 12 carbon atoms which is unsubstituted or substituted by halogen, hydroxy, cyano, tetrahydrofuryl or lower alkoxy; or are acyl of 1 to 12 carbon atoms, cycloalkyl of 5 to 10 carbon atoms or unsubstituted aralkyl or aryl, or aralkyl or aryl each substituted by halogen, cyano, nitro, trifluoromethyl, lower alkyl, lower alkoxy, lower alkoxycarbonyl, —NX'X"— or 4—NX'X—"phenylamino, wherein X' and X" are each independently of the other hydrogen, lower alkyl, cyclohexyl, benzyl or phenyl, or the pairs of substituents —NR$_1$R$_2$ and —NR$_3$R$_4$ are each a 5- or 6-membered, preferably saturated, heterocyclic radical, $V_1$ and $V_2$ are hydrogen, halogen, lower alkyl, $C_1$-$C_{12}$alkoxy, $C_1$-$C_{12}$-acyloxy, benzyl, phenyl, benzyloxy, phenyloxy, or benzyl or benzyloxy, each substituted by halogen, cyano, lower alkyl or lower alkoxy, or are the group —NT$_1$T$_2$, in which T$_1$ and T$_2$ are each independently of the other hydrogen, lower alkyl, $C_5$-$C_{10}$cycloalkyl, unsubstituted benzyl or benzyl which is substituted by halogen, cyano, lower alkyl or lower alkoxy, or are acyl of 1 to 8 carbon atoms, and T$_1$ is also unsubstituted phenyl or phenyl which is substituted by halogen, cyano, lower alkyl or lower alkoxy, and the rings $A_1$ and $A_2$ are each independently of the other an aromatic or heterocyclic radical of 6 ring atoms which may contain an aromatic fused ring, which rings $A_1$ and $A_2$ as well as the fused rings may be substituted.

These bisphthalide lactones can be used as color forming components in pressure-sensitive or heat-sensitive recording materials and, when used in conjunction with a condensation component and an acid developer, form intense colored images.

10 Claims, No Drawings

BISPHTHALIDE LACTONES, THEIR PREPARATION AND THE USE THEREOF IN RECORDING MATERIALS

The present invention relates to bisphthalide lactones, to their preparation and to the use thereof in heat-sensitive or pressure-sensitive recording materials.

The bisphthalide lactones of this invention have the general formula

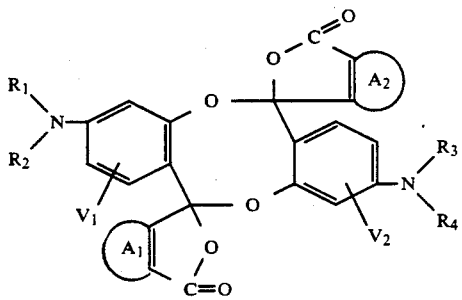

(I)

wherein $R_1$, $R_2$, $R_3$ and $R_4$ are each independently of one another hydrogen, alkyl of at most 12 carbon atoms which is unsubstituted or substituted by halogen, hydroxy, cyano, tetrahydrofuryl or lower alkoxy; or are acyl of 1 to 12 carbon atoms, cycloalkyl of 5 to 10 carbon atoms or unsubstituted aralkyl or aryl, or aralkyl or aryl each substituted by halogen, cyano, nitro, trifluoromethyl, lower alkyl, lower alkoxy, lower alkoxycarbonyl, NX'X''— or 4-NX'X''-phenylamino, wherein X' and X'' are each independently of the other hydrogen, lower alkyl, cyclohexyl, benzyl or phenyl, or the pairs of substituents —$NR_1R_2$ and —$NR_3R_4$ are each a 5- or 6-membered, preferably saturated, heterocyclic radical, $V_1$ and $V_2$ are hydrogen, halogen, lower alkyl, $C_1$–$C_{12}$alkoxy, $C_1$–$C_{12}$-acyloxy, benzyl, phenyl, benzyloxy, phenyloxy, or benzyl or benzyloxy each substituted by halogen, cyano, lower alkyl or lower alkoxy, or are the group —$NT_1T_2$, in which $T_1$ and $T_2$ are each independently of the other hydrogen, lower alkyl, $C_5$–$C_{10}$cycloalkyl, unsubstituted benzyl or benzyl which is substituted by halogen, cyano, lower alkyl or lower alkoxy, or are acyl of 1 to 8 carbon atoms, and $T_1$ is also unsubstituted phenyl or phenyl which is substituted by halogen, cyano, lower alkyl or lower alkoxy, and the rings $A_1$ and $A_2$ are each independently of the other an aromatic or heterocyclic radical of 6 ring atoms which may contain an aromatic fused ring, which rings $A_1$ and $A_2$ as well as the fused rings may be substituted.

Alkyl groups $R_1$, $R_2$, $R_3$ and $R_4$ may be straight chain or branched. Such alkyl groups are typically methyl, ethyl, n-propyl, isopropyl, n-butyl, 1-methylbutyl, sec-butyl, tert-butyl, amyl, isoamyl, n-hexyl, 2-ethylhexyl, n-heptyl, n-octyl, isooctyl, 1,1,3,3-tetramethylbutyl, n-nonyl, isononyl, 3-ethylheptyl, decyl or n-dodecyl.

Substituted alkyl groups $R_1$, $R_2$, $R_3$ and $R_4$ are preferably cyanoalkyl, haloalkyl, hydroxyalkyl or lower alkoxyalkyl, each preferably containing a total of 2 to 8 carbon atoms. Such substituted alkyl groups are, typically, cyanoethyl, 2-chloroethyl, 2-chloropropyl, 2-hydroxyethyl, 3-hydroxypropyl, 2-methoxyethyl, 2-ethoxyethyl, 2,3-dihydroxypropyl, 2-hydroxy-2-chloropropyl, 3-methoxypropyl, 4-methoxybutyl or 4-propoxybutyl as well as tetrahydrofurfuryl.

The R substituents and $T_1$ and $T_2$ defined as cycloalkyl are, typically, cyclopentyl, cycloheptyl or preferably cyclohexyl. The cycloalkyl radicals may contain one or more $C_1$–$C_4$alkyl groups, preferably methyl groups, and contain a total of 5 to 10 carbon atoms.

$R_1$, $R_2$, $R_3$ and $R_4$ defined as aralkyl may be phenethyl, phenylisopropyl or, preferably, benzyl. The radicals R defined as aryl are preferably naphthyl or, most preferably, phenyl.

Preferred substituents of the R substituents defined as aralkyl and aryl are halogen, cyano, methyl, trifluoromethyl, methoxy or carbomethoxy. Illustrative of such araliphatic and aromatic radicals are methylbenzyl, 2,4- or 2,5-dimethylbenzyl, chlorobenzyl, dichlorobenzyl, cyanobenzyl, tolyl, xylyl, chlorophenyl, methoxyphenyl, trifluoromethylphenyl, 2,6-dimethylphenyl or carbomethoxyphenyl.

A heterocyclic radical —$NR_1R_2$ and —$NR_3R_4$ may be pyrrolidino, piperidino, pipecolino, morpholino, thiomorpholino or piperazino, for example N-methylpiperazino or N-phenylpiperazino. Preferred saturated heterocyclic radicals —$NR_1R_2$ and —$NR_3R_4$ are pyrrolidino, piperidino or morpholino.

—$NR_1R_2$ and —$NR_3R_4$ are preferably identical.

The substituents $R_1$, $R_2$, $R_3$ and $R_4$ are preferably cyclohexyl, tolyl, benzyl, cyano-lower alkyl, for example 2-cyanoethyl or, preferably, lower alkyl such as methyl, ethyl, n-propyl, isopropyl, n-butyl or isoamyl.

—$NR_1R_2$ und —$NR_3R_4$ are preferably also pyrrolidino, N-lower alkyl-N-tetrahydrofurfurylamino, 4-di-lower alkylaminophenylamino or 4-(4'-phenylaminophenylamino)phenylamino.

An acyloxy radical $V_1$ and $V_2$ is typically formyloxy, lower alkylcarbonyloxy such as acetyloxy or propionyloxy, or benzoyloxy. $V_1$ and $V_2$ as $C_1$–$C_{12}$alkoxy may be a straightchain or branched group such as methoxy, ethoxy, isopropoxy, n-butoxy, tert-butoxy, amyloxy, 1,1,3,3-tetramethylbutoxy, n-hexyloxy, n-octyloxy or dodecyloxy.

$V_1$ and $V_2$ are conveniently hydrogen, halogen, lower alkyl such as methyl, benzyloxy, $C_1$–$C_8$alkoxy, preferably lower alkoxy such as methoxy, ethoxy, isopropoxy or tert-butoxy, or the group -$NT_1T_2$, wherein one of $T_1$ and $T_2$ is preferably $C_1$–$C_8$acyl or lower alkyl and the other is hydrogen or lower alkyl. The acyl radical is in this case preferably lower alkycarbonyl such as acetyl or propionyl. Preferably $V_1$ and $V_2$ are acetylamino, dimethylamino, diethylamino, benzyloxy or, more particularly, lower alkoxy and, most preferably, ethoxy or hydrogen.

$V_1$ and $V_2$ are preferably in ortho-position to —$NR_1R_2$ and —$NR_3R_4$.

A 6-membered aromatic ring $A_1$ and $A_2$ is preferably a benzene ring which is unsubstituted or substituted by halogen, cyano, nitro, lower alkyl, lower alkoxy, lower alkylthio, lower alkylcarbonyl, lower alkoxycarbonyl, amino, lower alkylamino, di-lower alkylamino or lower alkylcarbonylamino. A 6-membered heterocyclic ring $A_1$ and $A_2$ is preferably a nitrogen-containing heterocycle having aromaticity, for example a pyridine or pyrazine ring. The rings $A_1$ and $A_2$ may also contain a fused aromatic ring, preferably a benzene ring, and are thus, for example, a naphthalene, quinoline or quinoxaline ring.

The preferred 6-membered aromatic or heterocyclic radicals $A_1$ and $A_2$ are the 2,3-pyridino, 3,4-pyridino, 2,3-pyrazino, 2,3-quinoxalino, 1,2-naphthalino, 2,3-naphthalino or 1,2-benzo radical which is unsubstituted or substituted by halogen such as chloro or bromo, nitro, lower alkyl, lower alkoxy, lower alkylthio or an unsubstituted or substituted amino group as defined above. The unsubstituted 1,2-benzo radical or the 1,2-benzo radical which is substituted by 4 chlorine atoms is particularly preferred.

Acyl is preferably formyl, lower alkylcarbonyl such as acetyl or propionyl, or benzoyl. Further acyl radicals may be lower alkylsulfonyl such as methylsulfonyl or ethylsulfonyl, as well as phenylsulfonyl. Benzoyl and phenylsulfonyl may be substituted by halogen, methyl, methoxy or ethoxy.

Lower alkyl, lower alkoxy and lower alkylthio denote those groups or moieties which contain 1 to 6, preferably 1 to 3, carbon atoms. Illustrative of such groups are methyl, ethyl, n-propyl, isopropyl, n-butyl, sec-butyl, tert-butyl, amyl, isoamyl or hexyl; and methoxy, ethoxy, isopropoxy, isobutoxy, tert-butoxy or amyloxy; and methylthio, ethylthio, propylthio or butylthio.

Halogen is conveniently fluoro, bromo or, preferably, chloro.

Particularly important bisphthalide lactones are compounds of formula

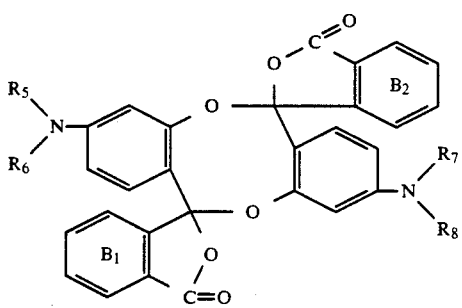

(2)

wherein $R_5$, $R_6$, $R_7$ and $R_8$ are each independently of one another $C_1-C_8$alkyl, $C_5-C_6$cycloalkyl or unsubstituted benzyl or phenyl, or benzyl or phenyl each substituted by halogen, lower alkyl, lower alkoxy or lower alkoxycarbonyl, or the pairs of substituents $-NR_5R_6$ and $-NR_7R_8$ are each independently of the other pyrrolidino, piperidino or morpholino, and the rings $B_1$ and $B_2$ are unsubstituted or substituted by halogen, lower alkyl, lower alkoxycarbonyl or di-lower alkylamino.

Among the bisphthalide lactones of formula (2), those compounds are especially preferred in which $R_5$, $R_6$, $R_7$ and $R_8$ are lower alkyl or benzyl and the rings $B_1$ and $B_2$ are unsubstituted or substituted by halogen, lower alkyl or dimethylamino.

Preferred bisphthalide lactones are compounds of formula

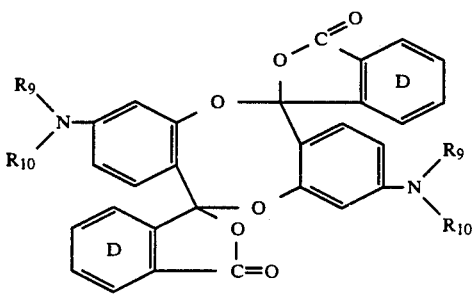

(3)

wherein $R_9$ is $C_1-C_6$alkyl, cyclohexyl, benzyl, phenyl, or methyl- or chloro-substituted benzyl or phenyl, and $R_{10}$ is $C_1-C_6$alkyl, benzyl, or chloro- or methyl-substituted benzyl, and the rings D are unsubstituted or substituted by 1 to 4 chlorine atoms.

Particularly preferred bisphthalide lactones of formula (3) are those wherein $R_9$ and $R_{10}$ are $C_1-C_4$alkyl and the benzene rings D are unsubstituted.

The bisphthalide lactones of formulae (1) to (3) are prepared by reacting a ketonic acid compound of formula

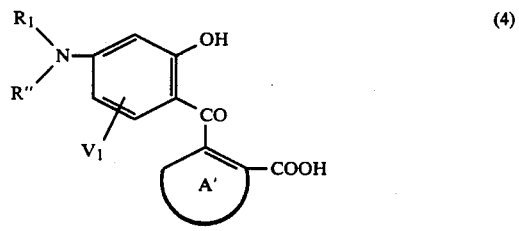

(4)

wherein $R'$, $R''$, $V'$ and $A'$ have the meanings of $R_1$, $R_2$, $R_3$, $R_4$, $V_1$, $V_2$, $A_1$ and $A_2$, individually or in the form of a mixture, in the presence of a dehydrating agent such as an acid anhydride of formula

$$Z-CO-O-CO-Z' \qquad (5)$$

wherein Z and Z' may be identical or different and are alkyl of 1 to 4 carbon atoms or phenyl, or an acid halide of formula

$$Z''-Q-Hal, \qquad (6)$$

wherein $Z''$ is halogen, alkyl of 1 to 4 carbon atoms or phenyl, and Q is $-CO-$, $-SO-$ or $-SO_2-$, and Hal is halogen.

The anhydrides of formula (5) may be used as mixed anhydrides, i.e. as anhydrides of two different acids. Exemplary of suitable acid halides of formula (6) are phosgene or, preferably, thionyl chloride.

The reaction is conveniently carried out in an anhydrous medium, for example in an excess of the anhydride employed, preferably acetic anhydride, or in an organic solvent such as benzene, toluene, xylene, nitrobenzene, chlorobenzene, acetonitrile, propionitrile or butyronitrile or, preferably, acetone, chloroform or methyl ethyl ketone.

The preparation of the lactones is conveniently carried out at a temperature of or below the boiling point of this solvent, preferably at a temperature in the range from 30° to 110° C., most preferably from 30° to 70° C.

The reaction time will depend on the temperature, the dehydrating agent, and on the solvent employed, and is normally from ½ hour to 5 hours, preferably from ¾ hour to 3 hours.

The isolation of the final product of formula (1) is carried out in conventionally known manner by isolating the precipitate, if necessary by addition of water, washing and drying, or by treatment with a suitable organic solvent such as methanol, isopropanol, acetone, chloroform or toluene, and, in this case, recrystallising the product.

The bisphthalide lactones of formulae (1) to (3) are normally colourless or, at most, weakly coloured compounds. When brought into contact together with a condensation component and a developer which is preferably acid, i.e. an electron acceptor, then depending on the condensation component and the developer, they immediately develop intense yellow, orange, red, violet, blue, green, grey or black images which are particularly fast to light and sublimation. A further possible combination comprises using the above ternary system together with one or more conventional colour formers such as 3,3-(bisaminophenyl)phthalides such as CVL, 3-indolyl-3-aminophenylaza- or -diazaphthalides, (3,3-bisindolyl)-phthalides, 3-aminofluorans, 6-dialkylamino-2-dibenzylaminofluorans, 6-dialkylamino-3-methyl-2-arylaminofluorans, 3,6-bisalkoxyfluorans, 3,6-bis(diarylamino)fluorans, leucoauramines, spiropyranes, spirodipyranes, chromenopyrazoles, chromenoindoles, phenoxazines, phenothiazines, quinazolines, rhodamine lactams, carbazolylmethanes or further triarylmethaneleuco dyes.

In conjunction with the condensation components, the developer and optional conventional colour formers, the bisphthalide lactones of this invention can be used in pressure-sensitive as well as in heat-sensitive recording materials.

Condensation components which may suitably be used are all coupling components common in azo chemistry and known from the literature, provided they contain no acid water-solubilising groups such as carboxyl and sulfo groups.

Illustrative examples of the great range of possibilities are: coupling components of the benzene series, of the naphthalene series, of the open-chain compounds containing active methylene groups, and of the heterocyclic series.

Representative examples of the cited coupling components are N-substituted aminophenylethylene compounds, N-substituted aminophenylstyrene compounds, acylacetarylamides, monohydric or polyhydric phenols, phenol ethers (phenetols), 3-aminophenol ether, anilines, naphthylamines, thionaphthenes, diarylamines, naphthols, naphtholcarboanilides, morpholines, pyrrolidines, piperidines, piperazines, aminopyrimidines, aminopyrazoles, pyrazolones, thiophenes, acridines, aminothiazoles, phenothiazines, pyridones, indoles, indolizines, quinolones, pyrimidones, barbituric acids, carbazoles, benzomorpholines, dihydroquinolines, tetrahydroquinolines, indolines, kairolines or julolidines.

Particularly preferred coupling components are anilines such as cresidines, phenetidines or N,N-di-lower alkylanilines, 2-lower alkylindoles, 3-lower alkylindoles or 2-phenylindoles which may each be N-substituted by $C_1-C_8$alkyl as well as 5-pyrazolones such as 1-phenyl-3-methyl-5-pyrazolone. Further preferred coupling components are 3-lower alkyl-6-lower alkoxy- or -6-di-lower alkylaminoindoles which may also each be N-substituted by $C_1-C_8$alkyl.

Specific examples of coupling components are 2-amino-4-methoxytoluene, 3-amino-4-methoxytoluene, 3-amino-4-methoxy-1-ethylbenzene, 1,4-dimethoxy-2-aminobenzene, N,N-dimethylaniline, N,N-diethylaniline, N,N-dibenzylaniline, 3-acetylamino-N,N-dipropylaniline, 3-n-butoxy-N,N-di-n-butylaniline, 2-methyl-5-acetyloxy-N,N-diethylaniline, 4-ethoxydiphenylamine, 3-ethoxy-N,N-dimethylaniline, m-phenetidine, 3-ethoxy-N,N-diethylaniline, 1,3-bis(dimethylamino)benzene, 3-hydroxy-N,N-(di-2-cyclohexylethyl)aminobenzene, 1,1-(4'-diethylaminophenyl)ethylene, 1-phenyl-3-methyl-5-pyrazolone, 1-phenyl-5-methyl-3-pyrazolone, 1-(2'-chlorophenyl)-5-methyl-3-pyrazolone, 2-phenyl-4,6-bis(methylamino)pyrimidine, N-ethylcarbazole, N-methylpyrrole, 2-methylindole, 2-phenylindole, 1,2-dimethylindole, 1-ethyl-2-methylindole, 1-n-octyl-2-methylindole, 1-methyl-2-phenylindole, 1-ethyl-2-phenylindole, 3-methyl-6-methoxyindole, 3-methyl-6-dimethylaminoindole, 1-ethyl-3-methyl-6-methoxyindole, 1-ethyl-3-methyl-6-dimethylaminoindole, α-naphthol, β-naphthol, α-naphthylamine, β-naphthylamine, 3-cyanoacetylaminophenol, thionaphthene, phenothiazine, 3-methyl-5-aminopyrazole, pyrimidyl-2-ethyl acetate, iminodibenzyl, 1-benzyl-2-methylindoline, 2,3,3-trimethylindolenine, benzthiazol-2-ylacetonitrile, 1,3,3-trimethyl-2-methylene-indoline, 1-ethyl-3-cyano-4-methyl-6-hydroxy-2-pyridone, 3-phenyl-4-methylindolizine, 2,3-diphenylindolizine.

The amounts in which the bisphthalides and condensation components are used are not critical; however, it is preferred to use stoichiometric amounts.

Both the bisphthalide lactones as well as the condensation components may be used in the recording material by themselves alone or in the form of a combination of two or more of the same.

The developers employed may suitably be the inorganic or organic colour developers customarily used in recording materials and which are capable of attracting electrons (electron acceptors).

Typical examples of inorganic developers are activated clay substances such as attapulgus clay, acid clay, bentonite, montmorillonite; activated clay such as acid-activated bentonite or montmorillonite as well as halloysite, kaolin, zeolith, silica, zirconium dioxide, alumina, aluminium sulfate, aluminium phosphate or zinc nitrate.

Preferred inorganic colour developers are Lewis acids such as aluminium chloride, aluminium bromide, zinc chloride, iron(III) chloride, tin tetrachloride, tin dichloride, tin tetrabromide, titanium tetrachloride, bismuth trichloride, telluryl dichloride or antimony pentachloride.

The organic colour developers employed may be solid carboxylic acids, preferably aliphatic dicarboxylic acids such as tartaric acid, oxalic acid, maleic acid, citric acid, citraconic acid or succinic acid, as well as alkylphenol acetylene resin, maleic acid/rosin resin, carboxy polymethylene or a partially or completely hydrolysed polymer of maleic anhydride with styrene, ethylene or vinyl methyl ether.

Particularly suitable colour developers are compounds containing a phenolic hydroxyl group. These compounds may be monohydric and polyhydric phenols. These phenols may be substituted by halogen atoms, carboxyl groups, alkyl radicals, aralkyl radicals such as α-methylbenzyl, α,α-di-methylbenzyl, aryl radicals, acyl radicals such as arylsulfonyl, or alkoxycarbonyl radicals or aralkoxycarbonyl radicals such as benzyloxycarbonyl.

Specific examples of phenols which are suitable developers are: 4-tert-butylphenol, 4-phenylphenol, methylenebis(p-phenylphenol), 4-hydroxydiphenyl ether, α-naphthol, β-naphthol, methyl or benzyl 4-hydroxybenzoate, methyl 2,4-dihydroxybenzoate, 4-hydroxydiphenylsulfone, 4'-hydroxy-4-methyldiphenylsulfone, 4'-hydroxy-4-isopropoxydiphenylsulfone, 4-hydroxyacetophenone, 2,4-dihydroxybenzophenone, 2,2'-dihydroxydiphenyl, 2,4-dihydroxydiphenylsulfone, 4,4'-cyclohexylidenediphenol, 4,4'-isopropylidenediphenol, 4,4'-isopropylidenebis(2-methylphenol), 4,4-bis(4-hydroxyphenyl)valeric acid, 1-phenyl-2,2-bis(4-hydroxyphenyl)butane, 1-phenyl-1,1-bis(4-hydroxyphenyl)butane, resorcinol, hydroquinone, pyrogallol, phloroglucinol, p-, m-, o-hydroxybenzoic acid, 3,5-di-(α-methylbenzyl)salicylic acid, 3,5-di(α,α-dimethylbenzyl)salicylic acid, salicylosalicylic acid, alkyl gallate, gallic acid, hydroxyphthalic acid, dimethyl hydroxyphthalate, 1-hydroxy-2-naphthoic acid or phenol/formaldehyde prepolymers which may also be modified with zink. The preferred cited carboxylic acids are the salicylic acid derivatives which are preferably used as zinc salts. Particularly preferred zinc salicylates are disclosed in European patent application 0 181 283 or German Offenlegungsschrift 2 242 250.

The developers may also be used in admixture with basically inert or almost inert pigment or other modifiers such as silica gel or UV absorbers such as 2-(2'-hydroxyphenyl)benzotriazoles, benzophenones, cyanoacrylates, or phenyl salicylates. Examples of pigments are: talcum, titanium dioxide, alumina, hydrated alumina, zinc oxide, chalk, clays such as kaolin, as well as organic pigments, for example urea/formaldehyde condensates (BET surface area 2-75 $m^2/g$) or melamine/formaldehyde condensates.

The ratio of the developer to the other two components depends on the nature of the three components, on the nature of the colour change, on the colour reaction temperature and, of course, also on the desired colour concentration. Satisfactory results are obtained by using the colour developing components in amounts of 0.1 parts by weight, preferably at least 0.5 to 100 parts by weight, per part of the bisphthalide lactones and the condensation components together.

For the pressure-sensitive recording material, both bisphthalide lactones as well as condensation components are preferably dissolved jointly or else separately in an organic solvent, and the resultant solutions are conveniently encapsulated by the methods described, for example, in U.S. Pat. Nos. 2,712,507, 2,800,457, 3,016,308, 3,429,827, 3,578,605 and 4,100,103 or in British patent specifications 989 264, 1 156 725, 1 301 052 or 1 355 124. Also suitable are microcapsules which are formed by interfacial polymerisation, for example capsules of polyester, polycarbonate, polysulfonamide, polysulfonate, preferably, however, of polyamide, polyurea or polyurethane. The encapsulation is usually necessary to separate the colour-forming components from the developer and thus to prevent a premature reaction. This separation can also be achieved by incorporating the colour-forming components in foam-like, sponge-like or honeycomb-like structures.

Illustrative of suitable solvents are preferably non-volatile solvents such as a halogenated benzene, diphenyl or paraffin, for example chloroparaffin, trichlorobenzene, monochlorodiphenyl, dichlorodiphenyl, or trichlorodiphenyl; an ester such as dibutyl adipate, dibutyl phthalate, dioctyl phthalate, butylbenzyl adipate, trichloroethylphosphate, trioctyl phosphate, tricresyl phosphate; an aromatic ether such as benzylphenyl ether; hydrocarbon oils such as paraffin oil or kerosene, aromatic hydrocarbons, for example an alkylated derivative, for example an isopropyl, isobutyl, sec-butyl or tert-butyl derivative, of diphenyl, naphthalene or terphenyl, dibenzyltoluene, a partially hydrognated terphenyl, a mono- to tetraalkylated diphenylalkane containing 1 to 3 carbon atoms in each of the alkyl moieties, dodecylbenzene, a benzylated xylene, phenyl xylyl ethane, or other chlorinated or hydrogenated condensed hydrocarbons. Mixtures of different solvents, especially mixtures of paraffin oils or kerosene and diisopropylnaphthalene or partially hydrogenated terphenyl, are often used to achieve an optimum solubility for the colour formation, a rapid and intense coloration, and a viscosity which is advantageous for the microencapsulation.

The microcapsules containing the colour-forming components can be used for the production of a very wide range of known kinds of pressure-sensitive copying materials. The various systems differ substantially from one another in the arrangement of the capsules and of the colour reactants, and in the nature of the support.

A preferred arrangement is that in which the encapsulated colour former is in the form of a layer on the back of a transfer sheet and the developer (electron acceptor) is in the form of a layer on the face of a receiver sheet. Another arrangement of the components is that wherein the microcapsules containing the colour-forming components and the developer are in or on the same sheet, in the form of one or more individual layers, or are incorporated in the substrate.

To obtain the desired colour, the capsule material which contains the colour-forming components can be mixed with other capsules which contain conventional colour formers. Similar results are obtained by encapsulating the colour-forming components jointly with one or more conventional colour formers.

The capsules are preferably secured to the support by means of a suitable binder. As paper is the preferred support, these binders are principally paper-coating agents, for example gum arabic, polyvinyl alcohol, hydroxymethylcellulose, casein, methyl cellulose, dextrin, starch or starch derivatives or polymer latices. These last mentioned substances are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers. The support may also be a plastic sheet.

The copying material preferably comprises a capsule-free layer which contains the colour-forming components and a colour developing layer containing, as colour developer, at least one inorganic metal salt of a polyvalent metal, preferably a halide or a nitrate, for example zinc chloride, tin chloride, zinc nitrate or a mixture thereof.

The ternary colour former system of this invention is particularly suitable for the production of a heat-sensitive recording material for use in thermography. In this utility, the three components come into contact with one another when heated to form a colour and develop images on the support.

The heat-sensitive recording material normally comprises at least one support, the three components and, in some cases, also a binder and/or wax. If desired, the recording material may additionally contain an activator, for example benzyl diphenyl, benzyloxy naphthalene, or a sensitiser.

Thermoreactive recording systems comprise, for example, heat-sensitive recording and copying materials and papers. These systems are used, typically, for recording information, for example in computers, printers, facsimile or copying machines, or in medical and technical recording and measuring instruments, as in electrocardiographs, or for marking labels or tickets (train or air tickets). The image formation (marking) can also be effected manually with a heated pen. Laser beams can also be used to produce heat-induced marks.

The thermoreactive recording material can be composed such that the colour forming components are dispersed or dissolved in one binder layer and the developer is dissolved or dispersed in the binder in a second layer. An alternative method comprises dispersing all three components in the same layer. By means of heat the layer or layers are softened or fused, whereupon the three components come into contact with one another at the areas where heat is applied and the desired colour develops at once.

Fusible, film-forming binders are preferably used for the preparation of the heat-sensitive recording material. These binders are normally water-soluble, whereas the three components are insoluble in water. The binder should be able to disperse the three components at room temperature and fix them on the support.

Examples of binders which are soluble, or at least swellable, in water are hydrophilic polymers such as polyvinyl alcohol, alkali metal polyacrylates, hydroxyethylcellulose, methyl cellulose, carboxmethylcellulose, polyacrylamide, polyvinyl pyrrolidone, carboxylated butadiene/styrene copolymers, gelatin, starch, or esterified corn starch.

If the three components are in two or three separate layers, it is possible to use water-insoluble binders, i.e. binders which are soluble in non-polar or only weakly polar solvents, for example natural rubber, synthetic rubber, chlorinated rubber, polystyrene, styrene/butadiene copolymers, polymethylacrylates, ethyl cellulose, nitrocellulose or polyvinyl carbazole. The preferred arrangement, however, is that in which all three components are contained in one layer in a water-soluble binder.

To ensure the stability of the heat-sensitive recording material or the density of the developed image, the material may be provided with an additional protective layer. Such protective layers consist as a rule of water-soluble and/or water-insoluble resins which are customary polymer materials or aqueous emulsions thereof.

Specific examples of water-soluble polymer materials are polyvinyl alcohol, starch, starch derivatives, cellulose derivatives such as methoxy cellulose, hydroxyethyl cellulose, carboxymethyl cellulose, methyl cellulose or ethyl cellulose, sodium polyacrylate, polyvinyl pyrrolidone, polyacrylamide/acrylate copolymers, acrylamide/acrylate/methacrylic acid copolymers, styrene/maleic anhydride copolymer alkali metal salts, isobutene/maleic anhydride copolymer alkali metal salts, polyacrylamide, sodium alginate, gelatin, casein, water-soluble polyesters or carboxyl-modified polyvinyl alcohol.

The following water-insoluble resins may in some cases be used in the protective coating in conjunction with the cited water-soluble polymer resins: polyvinyl acetate, polyurethanes, styrene/butadiene copolymers, polyacrylic acid, polyacrylates, vinyl chloride/vinyl acetate copolymers, vinyl alcohol/vinyl acetate/maleic acid terpolymers, polybutyl methacrylate, ethylene/vinyl acetate copolymers und styrene/butadiene/acrylate copolymers.

Both the thermoreactive coatings as well as the resin coatings may contain further modifiers. To enhance the degree of whiteness or the printability of the recording material and to prevent the heated nib or plate from sticking, these coatings may contain, for example, antioxidants, UV absorbers, solubilisers, talcum, titanium dioxide, zinc oxide, hydrated alumina, calcium carbonate (e.g. chalk), clays or also organic pigments, for example urea/formaldehyde polymers. In order to effect the colour formation only within a limited temperature range, it is possible to add substances such as urea, thiourea, diphenyl thiourea, acetamide, acetanilide, benzosulfanilide, bis(stearoyl)ethylenediamide, stearamide, phthalic anhydride, benzyl benzyloxybenzoate, metal stearates such as zinc stearate, phthalonitrile, dibenzyl terephthalate, dimethyl terephthalate or other suitable fusible products which induce the simultaneous melting of the colour former and the developer. Thermographic recording materials preferably contain waxes, e.g. carnauba wax, montan wax, paraffin wax, microwax, polyethylene wax, condensates of higher fatty acid amides and formaldehyde, or condensates of higher fatty acids and ethylenediamine.

To improve the usefulness of the thermochromatic materials, the three components can be encapsulated in microcapsules. To this end, any of the above mentioned per se known methods for encapsulating colour formers or other chemical agents in microcapsules can be employed.

In the following Preparatory Instructions and Examples, the percentages are by weight, unless otherwise stated. Parts are by weight.

EXAMPLE 1

15.6 g of 4-diethylamino-2-hydroxybenzophenone-2'-carboxylic acid are suspended in 100 ml of aceton and 30 ml of acetic anhydride at 20°–25° C. and the suspension is heated to 60° C. After stirring for 1 hour at 55°–60° C., the reaction mixture is allowed to cool and then poured into 70 ml of water, whereupon the temperature rises to 50° C. After cooling to 20° C. and then stirring for 1 hour, the precipitate is filtered with suction and dried, affording 5.7 g of a compound of formula

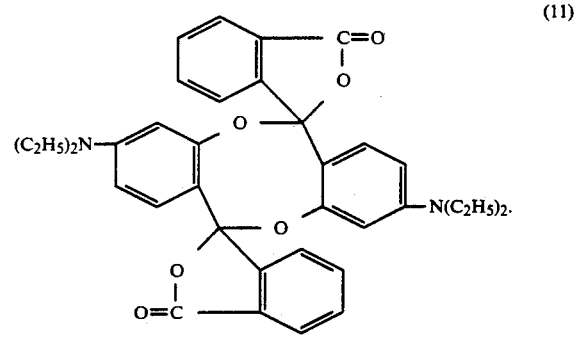

After recrystallisation from methyl ethyl ketone/petroleum ether, the compound has a melting point of 206°–207° C.

EXAMPLE 2

12.5 g of 4-diethylamino-2-hydroxybenzophenone-2'-carboxylic acid are stirred into 80 ml of chloroform. Then 5.1 ml of thionyl chloride are added dropwise over 10 minutes, the temperature rising from 25° to 36° C. After heating slowly to 50° C., a further 20 ml of chloroform are added and the temperature is kept at 50° C. for 2½ hours. Then a further 2.5 ml of thionyl chloride are added and the temperature is kept at 50° C. for another ½ hour. The suspension is filtered at 20° C. and the filter product is washed with chloroform and water and dried, to give 11.7 g of the compound of formula (11). After recrystallisation from toluene the compound has melting point of 206°–207° C.

EXAMPLE 3

11.2 g of 4-diethylamino-2-hydroxy-4'-tert-butylbenzophenone-2'-carboxylic acid are stirred into 60 ml of chloroform. Then 3.8 ml of thionyl chloride are added dropwise, the temperature rising to 35° C. The reaction mixture is heated to 50° C. and kept for 3 hours at this temperature, after which the evolution of gas has almost ceased. The solution is taken to dryness and the residue is treated with acetone. The crystals obtained are isolated by filtration, washed with acetone and dried, affording 3 g of a compound of formula

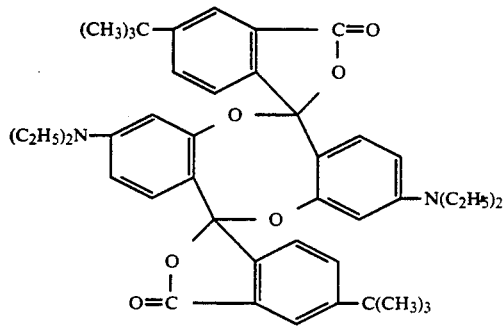
(12)

which melts at 178°–179° C.

EXAMPLE 4

14.8 g of 4-di-n-butylamino-2-hydroxybenzophenone-2'-carboxylic acid are suspended in 80 ml of acetone. To this suspension are added 24 ml of acetic anhydride and the reaction mixture is heated to reflux, stirred for 1½ hours and then allowed to cool. Then 70 ml of water are added and the batch is stirred overnight. The precipitate is isolated by filtration, washed with water and dried at 70°–80° C., affording 13.3 g of the compound of formula

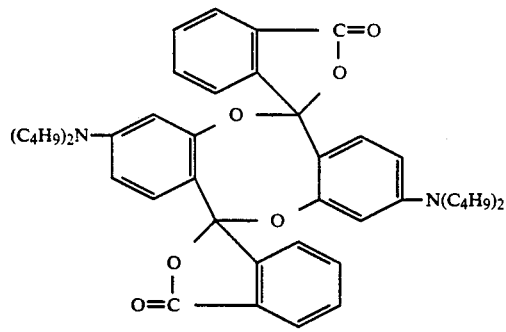
(13)

which melts at 150°–154° C.

EXAMPLE 5

A dispersion A is prepared by milling 6 g of the zinc salicylate of Example 1 of European patent application 0 181 283, 21 g of a 10% aqueous solution of polyvinyl alcohol (Polyviol V03/140) and 12 g of water with glass beads to a granular size of 2–4 μm.

A dispersion B is prepared by milling 0.87 g of the compound of formula (11) of Example 1, 5 g of a 10% aqueous solution of polyvinyl alcohol (Polyviol V03/140) and 2.9 g of water with glass beads to a granular size of 2–4 μm.

A dispersion C is prepared by milling 0.57 g of 2-phenylindole, 2 g of a 10% aqueous solution of polyvinyl alcohol (Polyviol V03/140) and 1.1 g of water with glass beads to a granular size of 2–4 μm.

Dispersions A, B and C are then mixed and applied with a doctor blade to paper having a basis weight of 50 g/m², such that the dry coating weight is 4 g/m². A lightfast black image develops when the paper is used in a facsimile machine (Infotec 6510).

EXAMPLE 6

0.15 g of the compound of formula (11) are dissolved in 10 g of diisopropylnaphthalene. Then 0.1 g of aminohydroquinone dimethyl ether (1,4-dimethoxy-2-aminobenzene) are likewise dissolved in 10 g of diisopropylnaphthalene and the two solutions are mixed at 25° C. The resultant mixture is applied with a printing roller to a sheet of paper which contains zink-2,5-bis-α-methylbenzylsalicylate. The paper is then subjected to a heat treatment for 1 minute at 150° C., whereupon an intense, lightfast yellow image with λmax. 420 nm develops.

EXAMPLE 7

The procedure of Example 6 is repeated, replacing aminohydroquinone dimethyl ether by 0.1 g of 2-phenyl-4,6-bis-N-methylaminopyrimidine. After the heat treatment, a red image develops with λmax. 580 nm.

EXAMPLE 8

The procedure of Example 6 is repeated, replacing aminohydroquinone dimethyl ether by 0.1 g of 2-phenylindole. After the heat treatment, a blue image develops with λmax. 600 nm.

EXAMPLE 9

To the mixture of dispersions A, B and C of Example 5 is added a dispersion D prepared from 1 g of 2-phenylamino-3-methyl-6-diethylaminofluoran, 3.5 g of a 10% aqueous solution of polyvinyl alcohol (Polyviol V03/140) and 2 g of water. The combined mixture is applied with doctor blade to a sheet of paper such that, after drying, the dry coating weight is 2.3 g/m². A grey-black copy of good lightfastness is obtained when the paper is used in a facsimile machine (Infotec 6510).

What is claimed is:

1. A bisphthalide lactone of formula

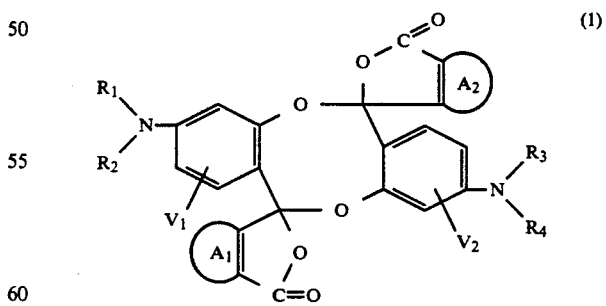
(1)

wherein $R_1$, $R_2$, $R_3$ and $R_4$ are each independently of one another hydrogen, alkyl of at most 12 carbon atoms which is unsubstituted or substituted by halogen, hydroxy, cyano, tetrahydrofuryl or lower alkoxy; or are acyl of 1 to 12 carbon atoms, cycloalkyl of 5 to 10 carbon atoms, phenyl, naphthyl, benzyl, phenethyl or phenylisopropyl, or aralkyl or aryl each substituted by halogen, cyano, nitro, trifluormethyl, lower alkyl, lower alkoxy, lower alkoxycarbonyl, —NX'X"— or 4-NX'X"-phenylamino, wherein X' and X" are each independently of the other hydrogen, lower alkyl, cyclohexyl, benzyl or phenyl, or the pairs of substituents —NR$_1$R$_2$ and —NR$_3$R$_4$ are each selected from the group consisting of pyrrolidino, piperidino, pipecolino, morpholino, thiomorpholino and piperazino, V$_1$ and V$_2$ are hydrogen, halogen, lower alkyl, C$_1$-C$_{12}$alkoxy, C$_1$-C$_{12}$-acyloxy, benzyl, phenyl, benzyloxy, phenyloxy, or benzyl or benzyloxy, each substituted by halogen, cyano, lower alkyl or lower alkoxy, or are the group —NT$_1$T$_2$, in which T$_1$ and T$_2$ are each independently of the other hydrogen, lower alkyl, C$_5$-C$_{10}$cycloalkyl, benzyl or benzyl which is substituted by halogen, cyano, lower alkyl or lower alkoxy, or are acyl of 1 to 8 carbon atoms, and T$_1$ is also phenyl or phenyl which is substituted by halogen, cyano, lower alkyl or lower alkoxy, and the rings A$_1$ and A$_2$ are each benzene.

2. A bisphthalide lactone according to claim 1, wherein —NR$_1$R$_2$ and —NR$_3$R$_4$ in formula (1) are identical.

3. A bisphthalide lactone according to claim 1, wherein R$_1$, R$_2$, R$_3$, R$_4$ are each independently of one another lower alkyl, cyano-lower alkyl, cyclohexyl, tolyl or benzyl, or —NR$_1$R$_2$ or —NR$_3$R$_4$ are pyrrolidino, N-lower alkyl-N-tetrahydrofurfurylamino, 4-di-lower alkylaminophenylamino or 4-(4'-phenylaminophenylamino)phenylamino.

4. A bisphthalide lactone according to claim 1, wherein V$_1$ and V$_2$ are hydrogen, halogen, lower alkyl, lower alkoxy or —NT$_1$T$_2$, and one of T$_1$ and T$_2$ is lower alkyl or C$_1$-C$_8$acyl and the other is hydrogen or lower alkyl.

5. A bisphthalide lactone according to claim 1, wherein the rings A$_1$ and A$_2$ are an unsubstituted or a substituted benzene, naphthalene, pyridine, pyrazine, quinoxaline or quinoline ring.

6. A bisphthalide lactone according to claim 1 of formula

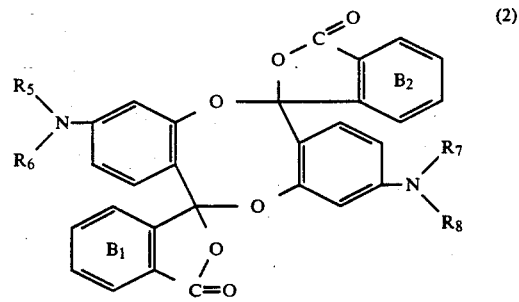

(2)

wherein R$_5$, R$_6$, R$_7$ and R$_8$ are each independently of one another C$_1$-C$_8$alkyl, C$_5$-C$_6$cycloalkyl, benzyl or phenyl, or benzyl or phenyl each substituted by halogen, lower alkyl, lower alkoxy or lower alkoxycarbonyl, or the pairs of substituents —NR$_5$R$_6$ and —NR$_7$R$_8$ are each independently of the other pyrrolidino, piperidino or morpholino, and the rings B$_1$ and B$_2$ are unsubstituted or substituted by halogen, lower alkyl, lower alkoxycarbonyl or di-lower alkylamino.

7. A bisphthalide lactone according to claim 6, wherein R$_5$, R$_6$, R$_7$ and R$_8$ are lower alkyl or benzyl, and the rings B$_1$ and B$_2$ are unsubstituted or substituted by halogen, lower alkyl or dimethylamino.

8. A bisphthalide lactone according to claim 7, wherein the rings B$_1$ and B$_2$ are substituted by tert.butyl.

9. A bisphthalide lactone according to claim 1 of formula

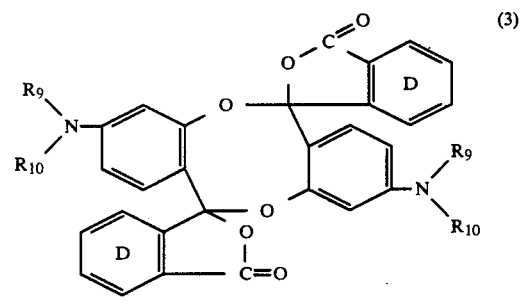

(3)

wherein R$_9$ is C$_1$-C$_6$alkyl, cyclohexyl, benzyl, phenyl, or methyl- or chloro-substituted benzyl or phenyl, and R$_{10}$ is C$_1$-C$_6$alkyl, benzyl, or chloro- or methyl-substituted benzyl, and the rings D are unsubstituted or substituted by 1 to 4 chlorine atoms.

10. A bisphthalide lactone according to claim 9, wherein R$_9$ and R$_{10}$ are C$_1$-C$_4$alkyl and the rings D are unsubstituted.

* * * * *